United States Patent [19]

Berg

[11] Patent Number: 4,975,157

[45] Date of Patent: Dec. 4, 1990

[54] SEPARATION OF LACTATE ESTERS BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 551,304

[22] Filed: Jul. 12, 1990

[51] Int. Cl.$^5$ .......................... B01D 3/40; C07C 69/68
[52] U.S. Cl. ........................................ 203/58; 203/60; 203/62; 203/64; 203/65; 560/179
[58] Field of Search ....................... 203/64, 62, 60, 58, 203/65; 560/179

[56] References Cited

U.S. PATENT DOCUMENTS

| | | | |
|---|---|---|---|
| 2,269,402 | 1/1942 | Swackhamer | 560/179 |
| 2,334,524 | 11/1943 | Wenker | 560/179 |
| 2,406,648 | 8/1946 | Weisberg et al. | 203/62 |
| 3,709,928 | 1/1973 | Murayama et al. | 203/64 |
| 3,736,236 | 5/1973 | DiFiore et al. | 203/64 |

FOREIGN PATENT DOCUMENTS 41-737  1/1966  Japan ................................... 560/179

Primary Examiner—Wilbur Bascomb

[57] ABSTRACT

The lower lactate esters are difficult to separate one from another by conventional distillation or rectification because of the close proximity of their boiling points. Lactate esters can be readily separated from each other by extractive distillation. Typical examples of effective agents are: for methyl lactate from ethyl lactate, ethylene glycol; ethyl lactate from isopropyl lactate, diethylene glycol; isopropyl lactate from n-propyl lactate, isophorone; n-propyl lactate from butyl lactate, 2-hydroxyacetophenone.

4 Claims, No Drawings

SEPARATION OF LACTATE ESTERS BY EXTRACTIVE DISTILLATION

FIELD OF THE INVENTION

This invention relates to a method for separating lactate esters one from another using certain oxygenated organic compounds as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Methyl lactate, B.P.=145° C. and ethyl lactate, B.P.=154° C. boil nine Celcius degrees apart and have a relative volatility of 1.2. Isopropyl lactate boils at 166° C. and its relative volatility with ethyl lactate is 1.10. n-Propyl lactate boils at 123° C. at 125 mm.Hg and its relative volatility with isopropyl lactate is 1.54. Butyl lactate boils at 185° C. and its relative volatility with n-propyl lactate is 2.29. Extractive distillation would be an attractive method of effecting the separation of the lactate esters one from another if agents can be found that (1) will enhance the relative volatility between the adjacent lactate esters and (2) are easy to recover from the lactates being separated, that is, form no azeotrope with the lactate and boil sufficiently above the lactate to make separation possible with only a few theoretical plates.

TABLE 1

Theoretical And Actual Plates Required vs. Relative Volatility For Lactate Separation

| Relative Volatility | Theoretical Plates Required At Total Reflux, 99% Purity | Actual Plates Required, 75% Eff. |
|---|---|---|
| 1.1 | 97 | 130 |
| 1.2 | 51 | 68 |
| 1.3 | 35 | 47 |
| 1.5 | 23 | 31 |
| 2.0 | 14 | 19 |
| 2.5 | 10 | 14 |
| 3.0 | 9 | 12 |

The advantage of using extractive distillation in this separation can be seen from the data shown in Table 1. The relative volatility of ethyl lactate to isopropyl lactate is 1.10 and thus require 97 theoretical plates for separation by conventional rectification at total reflux. Plates possessing an efficiency of 75% are commonly employed and thus 130 actual plates are required, clearly a very difficult separation. Several of the agents that I have discovered yield a relative volatility of about 1.3 which would reduce the plate requirement to only 47.

Extractive distillation typically requires the addition of an equal amount to twice as much extractive agent as the lactate esters on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible, with lactates otherwise it will form a two-phase azeotrope with the lactates in the recovery column and some other method of separation will have to be employed.

OBJECTIVE OF THE INVENTION

The objects of this invention are to provide a process or method of extractive distillation that will enhance the relative volatility of the lactate esters one from another in their separation in a rectification column. It is a further object of this invention to identify agents that are stable, can be separated from the lactates by rectification with relatively few plates and can be recycled to the extractive distillation column with little decomposition.

TABLE 2

Effective Agents For Separating Methyl Lactate from Ethyl Lactate

| Compound | Relative Volatility |
|---|---|
| None | 1.20 |
| Sulfolane | 1.48 |
| Ethylene glycol | 1.79 |
| 1,2-Butanediol | 2.32 |
| 1,5-Pentanediol | 1.54 |
| 1,6-Hexanediol | 1.46 |
| Diethylene glycol | 1.62 |
| Tetraethylene glycol | 1.66 |
| Polyethylene glycol 200 | 1.53 |
| Polyethylene glycol 300 | 1.52 |

TABLE 2-continued
Effective Agents For Separating
Methyl Lactate from Ethyl Lactate

| Compound | Relative Volatility |
| --- | --- |
| Dipropylene glycol | 1.61 |

TABLE 3
Ineffective Agents For Separating
Methyl Lactate From Ethyl Lactate

| Compound | Relative Volatility |
| --- | --- |
| Dimethylsulfoxide | Decomposes |
| Dimethylacetamide | Decomposes |
| Propylene carbonate | 1.2 |
| Propylene glycol | 1.26 |
| Triethylene glycol | 1.30 |
| 1,4-Butanediol | 1.35 |
| 1,3-Butanediol | 1.38 |

SUMMARY OF THE INVENTION

The objects of the invention are provided by a process for the separation of the lactate esters one from another which entails the use of certain oxygenated organic compounds as the agent in extractive distillation.

DETAILED DESCRIPTION OF THE INVENTION

I have discovered that certain oxygen containing compounds will effectively increase the relative volatility between methyl lactate and ethyl lactate and permit the separation of methyl lactate from ethyl lactate by rectification when employed as the agent in extractive distillation. Table 2 lists the agents that I have found to be effective. The data in Table 2 was obtained in a vapor-liquid equilibrium still at one atmosphere pressure. The relative volatilities are listed for each of the agents.

TABLE 4
Effective Agents For Separating
Ethyl Lactate From Isopropyl Lactate

| Compound | Relative Volatility |
| --- | --- |
| None | 1.10 |
| Diethylene glycol | 1.32 |
| Acetophenone | 1.28 |
| Isophorone | 1.23 |
| 2-Hydroxyacetophenone | 1.28 |
| n-Butyl benzoate | 1.21 |
| Methyl salicylate | 1.26 |

TABLE 5
Ineffective Agents For Separating
Ethyl Lactate From Isopropyl Lactate

| | |
| --- | --- |
| Ethylene glycol | Propylene glycol |
| 1,3-Butanediol | 1,4-Butanediol |
| 1,2-Butanediol | Dipropylene glycol |
| Triethylene glycol | 1,6-Hexanediol |
| Polyethylene glycol 200 | Polyethylene glycol 300 |
| Tripropylene glycol | Dimethylsulfoxide |
| Propylene carbonate | Dihexyl phthalate |
| Adiponitrile | Methyl benzoate |
| Benzonitrile | Propiophenone |
| Nitrobenzene | 2-Undecanone |
| Ethyl benzoate | Dipropylene glycol dibenzoate |
| Ethyl salicylate | Diethylene glycol dibenzoate |

TABLE 5-continued
Ineffective Agents For Separating
Ethyl Lactate From Isopropyl Lactate Benzyl butyl phthalate The compounds which are effective are ethylene glycol, 1,2-butanediol, 1,5-pentanediol, 1,6-hexanediol, diethylene glycol, tetraethylene glycol, polyethylene glycol 200, polyethylene glycol 300, dipropylene glycol and sulfolane.

Table 4 lists the agents that I have found to be effective in increasing the relative volatility of ethyl lactate to isopropyl lactate. The data in Table 4 was obtained in a vapor-liquid equilibrium still operated at 60 mm. Hg pressure. The compounds which are effective are diethylene glycol, acetophenone, isophorone, 2-hydroxyacetophenone, n-butyl benzoate and methyl salicylate.

Tables 3 and 5 list a number of compounds that were investigated but turned out to be ineffective in separating the methyl, ethyl and/or isopropyl lactates.

TABLE 6
Effective Agents For Separating
Isopropyl Lactate From n-Propyl Lactate

| Compound | Relative Volatility |
| --- | --- |
| None | 1.54 |
| Methyl salicylate | 2.24 |
| Butyl benzoate | 2.26 |
| 2-Hydroxyacetophenone | 2.36 |
| Isophorone | 2.61 |

TABLE 7
Effective Agents For Separating
n-Propyl Lactate From Butyl Lactate

| Compound | Relative Volatility |
| --- | --- |
| None | 2.29 |
| 2-Hydroxyacetophenone | 3.42 |
| Butyl benzoate | 5.20 |

Table 6 lists the agents that I have found to be effective in increasing the relative volatility of isopropyl lactate to n-propyl lactate and Table 7 lists the effective agents for n-propyl lactate from butyl lactate. The data in Tables 6 and 7 was obtained in a vapor-liquid equilibrium still operated at 60 mm. Hg. pressure. The compounds which are effective in separating isopropyl lactate from n-propyl lactate are methyl salicylate, butyl benzoate, 2-hydroxyacetophenone and isophorone. The compounds which are effective in separating n-propyl lactate from butyl lactate are 2-hydroxyacetophenone and butyl benzoate.

THE USEFULNESS OF THE INVENTION

The usefulness or utility of this invention can be demonstrated by referring to the data presented in Tables 2, 4, 6 and 7. All of the successful agents show that methyl lactate, ethyl lactate, isopropyl lactate, n-propyl lactate and butyl lactate can be separated one from the other by means of extractive distillation in a rectification column and that the ease of separation as measured by relative volatility is considerable.

WORKING EXAMPLES

EXAMPLE 1

Fifteen grams of methyl lactate, 25 grams of ethyl lactate and 20 grams of ethylene glycol were charged to a vapor-liquid equilibrium still and refluxed for four hours at 1 Atm. Analysis indicated a vapor composition of 14.6% methyl lactate, 85.4% ethyl lactate; a liquid composition of 8.7% methyl lactate, 91.3% ethyl lactate which is a relative volatility of 1.79.

EXAMPLE 2

150 ml. of methyl lactate and 250 ml. of ethyl lactate were placed in the stillpot of a 7.3 theoretical plate rectification column and heated. When refluxing began, an extractive agent comprising dipropylene glycol was pumped into the column at a rate of 15 ml/min. The temperature of the extractive agent as it entered the column was 95° C. After establishing the feed rate of the extractive agent, the heat input to the column was adjusted to give a total reflux rate of 40 ml/min. After two hours of operation, overhead and bottoms samples were collected and analysed by gas chromatography. The overhead analysis was 88.3% methyl lactate, 11.7% ethyl lactate and the bottoms analysis was 19.9% methyl lactate, 80.1% ethyl lactate. Using these compositions in the Fenske equation, with the number of theoretical plates in the column being 7.3, gave an average relative volatility of 1.60 for each theoretical plate.

EXAMPLE 3

Twenty grams of ethyl lactate, 10 grams of isopropyl lactate and 20 grams of diethylene glycol were charged to the vapor-liquid equilibrium still and refluxed for one hour at 60 mm. Hg pressure. Analysis indicated a vapor composition of 74.4% ethyl lactate, 25.6% isopropyl lactate; a liquid composition of 79.4% ethyl lactate, 20.6% isopropyl lactate which is a relative volatility of 1.32.

EXAMPLE 4

Thirty grams of isopropyl lactate, 10 grams of n-propyl lactate and 20 grams of isophorone were charged to a vapor-liquid equilibrium still and refluxed for one hour at 60 mm. Hg pressure. Analysis indicated a vapor composition of 88.5% isopropyl lactate, 11.5% n-propyl lactate; a liquid composition of 74.7% isopropyl lactate, 25.3% n-propyl lactate which is relative volatility of 2.61.

EXAMPLE 5

Ten grams of n-propyl lactate, 30 grams of butyl lactate and 20 grams of 2-hydroxyacetophenone were charged to the vapor-liquid equilibrium still and refluxed for 1.5 hours at 60 mm. Hg pressure. Analysis indicated a vapor composition of 29.3% n-propyl lactate, 70.7% butyl lactate; a liquid composition of 10.8% n-propyl lactate, 89.2% butyl lactate which is a relative volatility of 3.42.

I claim:

1. A method for recovering methyl lactate from a mixture of methyl lactate and ethyl lactate which comprises distilling a mixture of methyl lactate and ethyl lactate in the presence of about one part of an extractive agent per part of methyl lactate—ethyl lactate mixture, recovering methyl lactate as overhead product and obtaining the ethyl lactate and the extractive agent from the stillpot, wherein said extractive agent comprises one material selected from the group consisting of ethylene glycol, 1,2-butanediol, 1,5-pentanediol, 1,6-hexanediol, diethylene glycol, tetraethylene glycol, polyethylene glycol 200, polyethylene glycol 300, dipropylene glycol and sulfolane.

2. A method for recovering ethyl lactate from a mixture of ethyl lactate and isopropyl lactate which comprises distilling a mixture of ethyl lactate and isopropyl lactate in the presence of about one part of an extractive agent per part of ethyl lactate—isopropyl lactate mixture, recovering ethyl lactate as overhead product and obtaining the isopropyl lactate and the extractive agent from the stillpot, wherein said extractive agent comprises one material selected from the group consisting of diethylene glycol, acetophenone, isophorone, n-butyl benzoate, 2-hydroxyacetophenone and methyl salicylate.

3. A method for recovering isopropyl lactate from a mixture of isopropyl lactate and n-propyl lactate which comprises distilling a mixture of isopropyl lactate and n-propyl lactate in the presence of about one part of an extractive agent per part of isopropyl lactate—n-propyl lactate mixture, recovering isopropyl lactate as overhead product and obtaining the n-propyl lactate and the extractive agent from the stillpot, wherein said extractive agent comprises one material selected from the group consisting of methyl salicylate, butyl benzoate, 2-hydroxyacetophenone and isophorone.

4. A method for recovering n-propyl lactate from a mixture of n-propyl lactate and butyl lactate which comprises distilling a mixture of n-propyl lactate and butyl lactate in the presence of about one part of an extractive agent per part of n-propyl lactate—butyl lactate mixture, recovering n-propyl lactate as overhead product and obtaining the butyl lactate and the extractive agent from the stillpot, wherein said extractive agent is butyl benzoate or 2-hydroxyacetophenone.

* * * * *